United States Patent
McGregor

(10) Patent No.: US 10,908,314 B1
(45) Date of Patent: Feb. 2, 2021

(54) METHOD AND APPARATUS FOR MAPPING A CRUSH ZONE OF A PERFORATED CORE SAMPLE

(71) Applicant: Halliburton Energy Services, Inc., Houston, TX (US)

(72) Inventor: Jacob Andrew McGregor, Fort Worth, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 16/787,545

(22) Filed: Feb. 11, 2020

(51) Int. Cl.
*G01V 5/04* (2006.01)
*G01N 23/046* (2018.01)
(Continued)

(52) U.S. Cl.
CPC .............. *G01V 5/045* (2013.01); *G01N 1/286* (2013.01); *G01N 1/34* (2013.01); *G01N 15/08* (2013.01);
(Continued)

(58) Field of Classification Search
CPC ............ G01N 1/28; G01N 1/286; G01N 1/34; G01N 15/00; G01N 15/08; G01N 15/0806; G01N 15/088; G01N 2015/0061; G01N 2015/0096; G01N 2015/0833; G01N 2015/0846; G01N 23/046; G01N 23/06; G01N 23/083; G01N 23/18; G01N 2291/023; G01N 2291/0231; G01N 2291/024; G01N 2291/02458; G01N 2291/0258; G01N 2291/0289; G01N 2291/2636; G01N 2291/2638; G01N 2223/03; G01N 2223/04;
(Continued)

(56) References Cited

U.S. PATENT DOCUMENTS 5,331,155 A * 7/1994 Blauch .................... E21B 47/11
250/255

FOREIGN PATENT DOCUMENTS

WO WO-2014158139 A1 * 10/2014 ............. G01N 23/04

OTHER PUBLICATIONS

"Recommended Practices for Evaluation of Well Perforators," American Petroleum Institute, Sep. 2006, 66 pages.
(Continued)

*Primary Examiner* — Anastasia Midkiff
(74) *Attorney, Agent, or Firm* — John Wustenberg; Parker Justiss, P.C.

(57) ABSTRACT

Aspects of a method for mapping a perforation tunnel and crush zone of a perforated core sample. The method may include scanning a perforated core sample having a perforation tunnel containing a permeability-impairing material with a first computerized tomography (CT) scanning apparatus to produce a first 3D model of the perforation tunnel. The method may further include forming a cleared perforation tunnel by removing at least a portion of the permeability-impairing material from within the perforation tunnel without splitting the core sample at the perforation tunnel, and scanning the perforated core sample having the cleared perforation tunnel with a second computerized tomography (CT) scanning apparatus to produce a second 3D model of the cleared perforation tunnel. The method may compare the first 3D model and the second 3D model to obtain a 3D mapping of the perforation tunnel or a crush zone.

20 Claims, 5 Drawing Sheets

(51) Int. Cl.
  *G01N 23/06* (2018.01)
  *G01N 1/28* (2006.01)
  *G01N 1/34* (2006.01)
  *G01N 15/08* (2006.01)
  *G01N 23/18* (2018.01)

(52) U.S. Cl.
  CPC ....... *G01N 15/0806* (2013.01); *G01N 23/046* (2013.01); *G01N 23/06* (2013.01); *G01N 23/18* (2013.01); *G01V 5/04* (2013.01); *G01N 2015/0846* (2013.01); *G01N 2223/405* (2013.01); *G01N 2223/419* (2013.01); *G01N 2223/425* (2013.01)

(58) Field of Classification Search
  CPC ....... G01N 2223/1016; G01N 2223/30; G01N 2223/302; G01N 2223/303; G01N 2223/40; G01N 2223/405; G01N 2223/419; G01N 2223/425; G01N 2223/60; G01N 2223/615; G01N 2223/616; G01N 2223/648; G01N 2223/649; G01N 2223/65; G01N 2223/652; G01V 5/00; G01V 5/04; G01V 5/045; G01V 5/08; G01V 5/12

See application file for complete search history.

(56) References Cited

OTHER PUBLICATIONS

Grove B., et al., "An Improved Technique for Interpreting Perforating-Flow-Laboratory Results: Honoring Observed Cleanup Mechanisms," SPE 143998, Jun. 2012 SPE Drilling & Completion, Society of Petroleum Engineers, pp. 233-240.

Satti, R., et al., "From Computerized Tomography to CFD: Production Flow Prediction in Realistic Perforation Tunnels," SPE-174244-MS, Society of Petroleum Engineers, SPE European Formation Damage Conference and Exhibition, Jun. 3-5, 2015, 16 pages.

* cited by examiner

US 10,908,314 B1

METHOD AND APPARATUS FOR MAPPING A CRUSH ZONE OF A PERFORATED CORE SAMPLE

BACKGROUND

In order to predict a well's production, plan for well construction, and among other things, design a perforation tool and/or a downhole perforation procedure, one or more rock core samples that are considered to be representative of the subterranean formation may be tested in a laboratory setting. In one such test, a perforated core is split in order to take caliper measurements to assess the two-dimensional thickness of a crushed zone. Such testing assists in determining certain parameters of the subterranean formation and/or interactions between the explosive charges and the subterranean formation. The test results may be used in designing the wellbore, perforation tool and/or the downhole perforation procedure.

BRIEF DESCRIPTION

Reference is now made to the following descriptions taken in conjunction with the accompanying drawings, in which.

DETAILED DESCRIPTION

Disclosed herein in one embodiment is a method for mapping a perforation tunnel and crush zone of a core sample that provides a 3D mapping and geometry of the crush zone while leaving the core sample intact (e.g., at least without splitting the core sample at the perforation). Computerized tomography (CT) scans may be taken to obtain 3D mappings before and after removing a permeability-impairing material from the perforation, and aligning and comparing the 3D mappings to obtain the true 3D variable-thickness profile of the perforation's crushed-zone and permeability-impairing material impaired region. The method for mapping a perforation tunnel and crush zone may be used in determining a permeability of a crush zone of a perforated core sample, which is disclosed herein in another embodiment. Both methods are highly useful in the testing of the effectiveness of a shaped charge and/or determining characteristics, such as permeability, for a subterranean formation. The methods according to the disclosure allow the user to better understand the impaired permeability of the crush zone of the subterranean formation. A better understanding of the impaired permeability of the crush zone may, in turn, be used to better assess the economics of a given production (or injection) well, as the crush zone has a significant impact on the pressure-flow relationship of the well.

Figure 1:
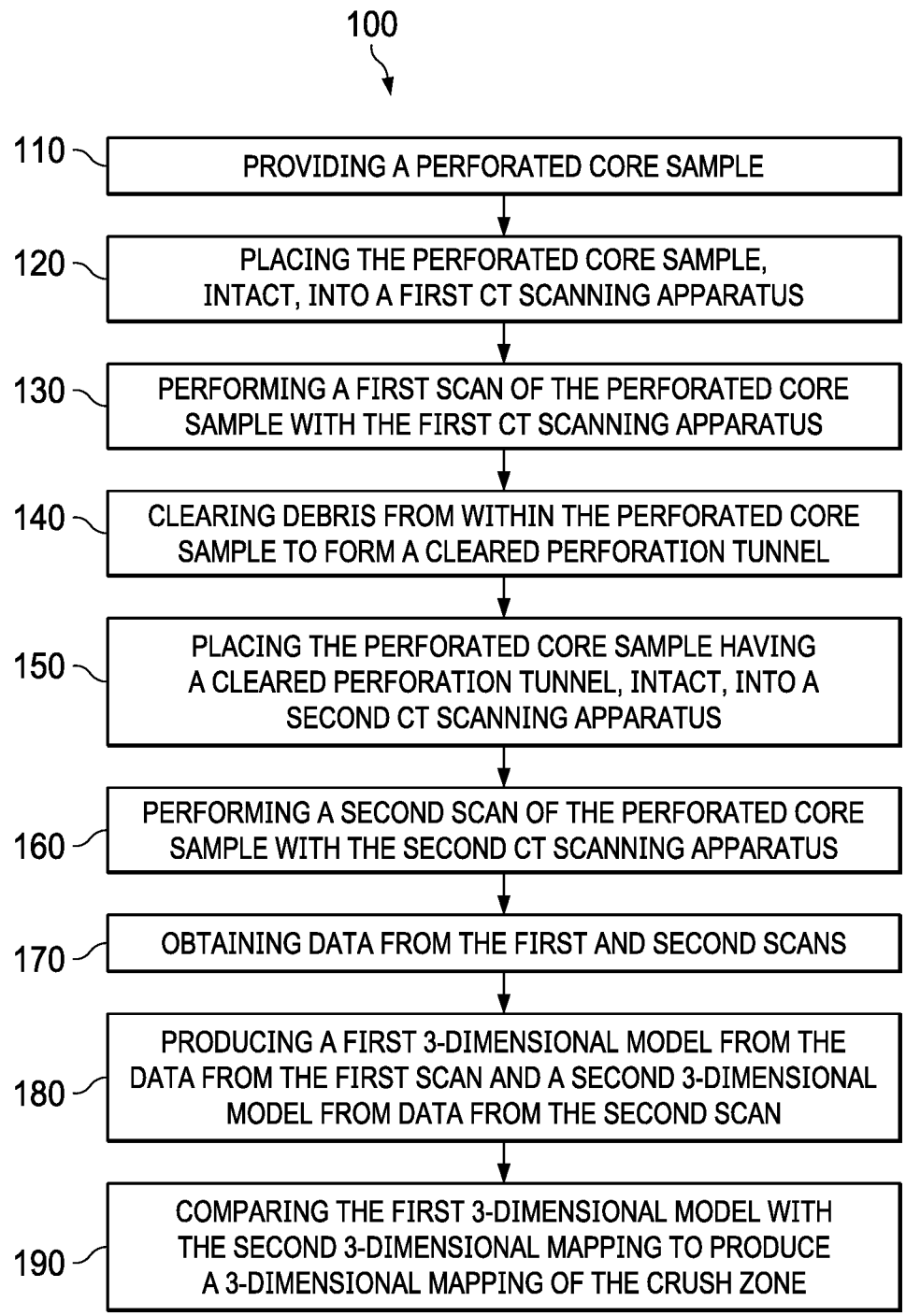
FIG. 1 is a flowchart of a method for mapping a perforation tunnel and crush zone of a perforated core sample.

FIG. 1 is a flowchart 100 of a method for mapping a perforation tunnel and crush zone of a perforated core sample. In one step 110, a perforated core sample is obtained, such as by perforating a previously unaltered core sample to form the perforated core sample. The core sample may be perforated in any manner suitable for testing purposes, such as by following American Petroleum Institute (API) RP 19B, Section 2 and Section 4. In a subsequent step 120, an unaltered and intact (e.g., not cut or split open) perforated core sample is placed into a first computerized tomography (CT) scanning apparatus. In a step 130, a first scan of the perforated core sample having the perforation tunnel is taken with the first computerized tomography (CT) scanning apparatus. The first scan, in the illustrated embodiment, may be used to produce a first 3D model of the perforation tunnel. In some embodiments, in order to obtain a mapping of the perforation tunnel as "open" (e.g., wherein the perforation tunnel has at least a partial opening at its open perforated end) the open perforated end of the tunnel may need to be lightly flushed with a fluid to remove any loose material present from the perforation process. The fluid, in one embodiment, may be a gas or liquid sufficient to remove loose material residing within the perforation tunnel, and may be used prior to the first scan.

In a next step 140, the perforated core sample is removed from the first computerized tomography (CT) scanning apparatus and permeability-impairing material is cleared from within the perforation tunnel without opening, altering or splitting the perforated core sample. The permeability-impairing material may include, in some examples, any permeability-impairing material that would impair permeability of the crush zone, including any liner material originating from shaped charges used in the perforation process, and the crushed-zone material lining the perforation tunnel. In some embodiments, the permeability-impairing material is mechanically cleared by scraping or scrubbing the permeability-impairing material from within the perforation tunnel.

In some embodiments, the permeability-impairing material is cleared using a brush mounted onto a drill or rotary tool, wherein the brush may be rotated while sweeping into and out of the perforation tunnel. In some embodiments, the brush may be a cylindrical brush of varying sizes. Depending on the type of rock or porous medium the core sample was taken from, the type of brush may vary. For example, for certain types of rock, the brush may be a nylon brush (e.g., if the rock may be from a softer rock formation). For rock formations that are harder rock, the brush may be a stainless steel brush or another type of durable brush. The size, both in length and width (or diameter), of the brush may also vary.

What results is a cleared perforation tunnel having at least some percentage of the permeability impairing material removed therefrom, such that an acceptable 3D mapping of the perforation tunnel may be obtained. The cleared perforation tunnel need not be 100% cleared of the permeability impairing material to obtain an acceptable 3D mapping of the perforation tunnel. However, typically the more permeability impairing material that is removed from the perforation tunnel, the better. In one or more examples, the cleared perforation tunnel has greater than 50% by volume of the permeability impairing material removed therefrom. In one or more other examples, the cleared perforation tunnel has greater than 75% by volume of the permeability impairing material removed therefrom, and in yet one or more other examples the cleared perforation tunnel has greater than 90% by volume of the permeability impairing material removed therefrom.

In a next step 150, after the permeability-impairing material is cleared from within the perforation tunnel, the perforated core sample having the cleared perforation tunnel may be placed into a second computerized tomography (CT) scanning apparatus. In one embodiment, the first and second computerized tomography (CT) scanning apparatuses are the same type, or actually the exact same computerized tomography (CT) scanning apparatus. In another embodiment the first and second computerized tomography (CT) scanning apparatuses are the same type, but different computerized tomography (CT) scanning apparatuses. In yet another embodiment, the first and second computerized tomography (CT) scanning apparatuses are different types of computerized tomography (CT) scanning apparatuses.

In a step 160, a second scan of the perforated core sample having the cleared perforation tunnel is taken with the second computerized tomography (CT) scanning apparatus. The second scan, in this embodiment, may be used to produce a second 3D model of the cleared perforation tunnel. In a next step 170, data is obtained from the first and second computerized tomography (CT) scans. In some embodiments, in a step 180, a first 3D model of the perforation tunnel may be made from the data from the first scan. The first 3D model may include spatial coordinates of the uncleared perforation tunnel. Further to step 180, a second 3D model of the cleared perforation tunnel may be made from the data of the second scan. The second 3D model may include spatial coordinates of the cleared perforation tunnel.

In a next step 190, the first 3D model is compared with the second 3D model to obtain a 3D mapping of the crush zone. The 3D mapping, in one embodiment, is a 3D variable-thickness profile of a crushed-zone region and a permeability-impairing material impaired region of the perforation tunnel. In some embodiments, the first 3D model is compared with the second 3D model by overlaying the first 3D model and the second 3D model using a fluid dynamics modeling tool. In some embodiments, the fluid dynamics modeling tool may be (or may be similar to) a Computational Fluid Dynamics (CFD) software tool such as, in one example, an ANSYS Fluent software tool.

Figure 2:
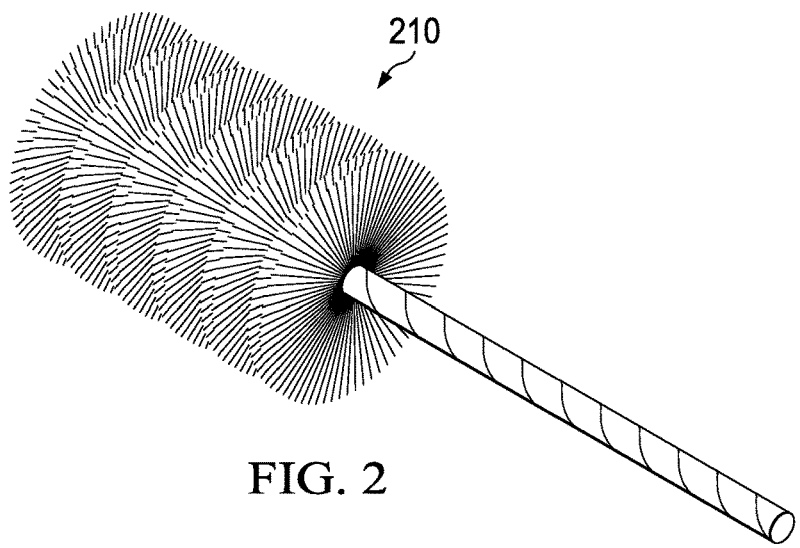
FIG. 2 is a perspective view of a brush that may be used to clear permeability-impairing material from the perforated core sample of FIG. 1.
Figure 3:
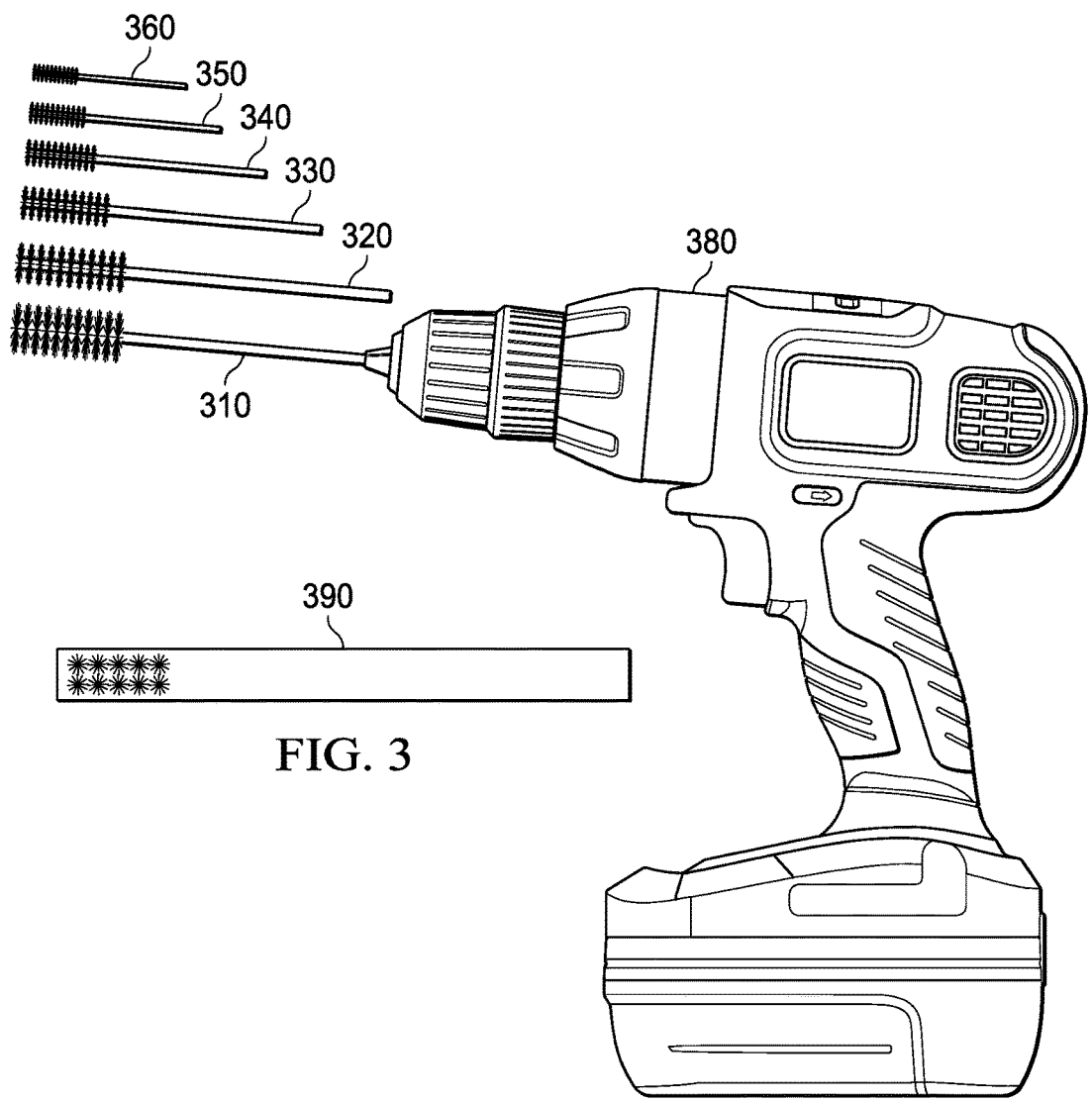
FIG. 3 is a representative drawing of a rotary tool and a plurality of brushes interchangeably usable with the rotary tool, which may be used to clear permeability-impairing material from the perforation tunnel.

Referring now to FIGS. 2 and 3, there are shown various embodiments of cleaning tools which may be used, in some embodiments, for example in step 140 discussed above. FIG. 2 is a perspective view of a brush 210 that may be used to clear permeability-impairing material from the perforated core sample such as described in FIG. 1. FIG. 3 is a representative drawing of a rotary tool 380 and a plurality of brushes 310-360 interchangeably usable with the rotary tool 380, which may be used to clear permeability-impairing material from the perforation tunnel. The rotary tool 380 in this example is a hand drill. Nevertheless, other rotary tools are within the scope of the disclosure. In one embodiment, a cylindrical wire brush, such as brush 310 may be attached with and driven by the rotary tool 380. The brush 310 may be inserted into the open planar end of the perforated-end of the core sample. The brush 310 may be rotated by the rotary tool 380 and swept into and out of the perforation tunnel to remove any permeability-impairing material. FIG. 3 additionally illustrates a hand brush 390, which could be used in those scenarios where the rotary tool 380 is not necessary, or possible, to use.

Figure 4:
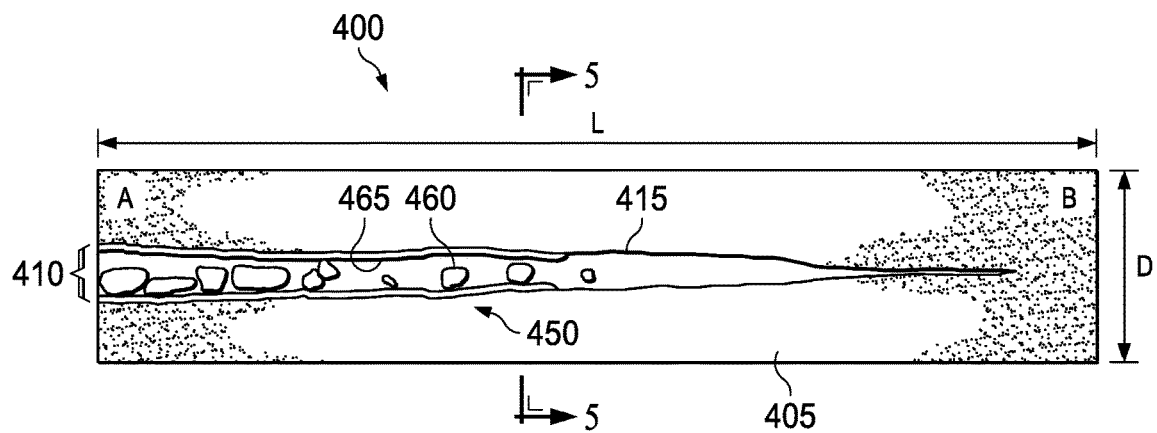
FIG. 4 is a cross-sectional view of a first computerized tomography (CT) scan of an intact perforated core sample having permeability-impairing material therein.

FIGS. 4-7 show images of a perforation tunnel along the crush zone of a perforated core sample before and after removing permeability-impairing material from the tunnel according to the disclosure. FIG. 4 is a cross-sectional view of a first computerized tomography (CT) scan of an intact perforated core sample 400 having permeability-impairing material 450 therein. The intact perforated core sample 400 includes the core material 405 (the sampled material from the formation, e.g. rock) and a perforation 410 extending from a perforated end (A) toward an unperforated end (B), which may be somewhat centrally located within the core sample having a length (L) and diameter (D). In the illustrated embodiment, the perforation extends only along a portion of the length (L) of the core sample 400. The perforation 410 may have been formed by an explosive shape charge as generally understood in the art, such that the perforated core sample 400 defines a generally elongate perforation tunnel 415. The perforation tunnel 415 contains the permeability-impairing material, as conceptually illustrated and generally indicated at 450. The permeability-impairing material 450 may include, by way of example, one or both of a liner material 460 and crushed zone material 465 originating from the jet of the shaped charge, lining the perforation tunnel 415.

Figure 5:
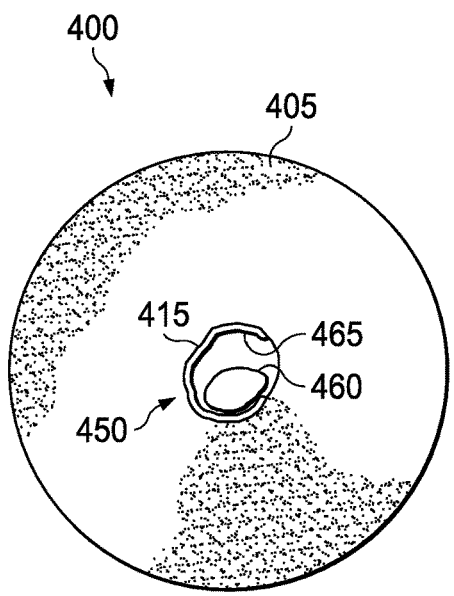
FIG. 5 is an alternative cross-sectional view of the first computerized tomography (CT) scan of the intact perforated core sample taken through the line 5-5 in FIG. 4.

FIG. 5 is an alternative cross-sectional view of the first computerized tomography (CT) scan of the intact perforated core sample 400 taken through the line 5-5 in FIG. 4. The views shown in FIGS. 4 and 5 may represent computerized tomography (CT) scans taken during a first computerized tomography (CT) scan of the perforated core sample 400 prior to clearing the perforation tunnel 415, such as per step 130 in the method of FIG. 1. Although conceptually shown and not to scale, both the liner material 460 and the crushed zone material 465 may impair the permeability of the core material 405 at the site of the perforation, thus undesirably impeding the flow of formation fluids in a perforated wellbore represented by the core sample 400. To assess the efficacy of the perforation and the effect of this permeability-impairing material, the permeability-impairing material 450 can be removed, such as exemplified in step 140 of FIG. 1, to clear the perforation tunnel 415 according to this disclosure.

Figure 7:
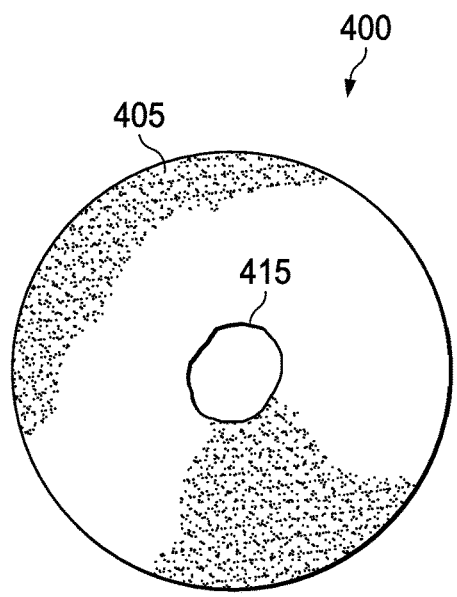
FIG. 7 is an alternative cross-sectional view of the second computerized tomography (CT) scan of the intact perforated core sample showing the cleared perforation tunnel, taken through the line 7-7 in FIG. 6.
Figure 6:
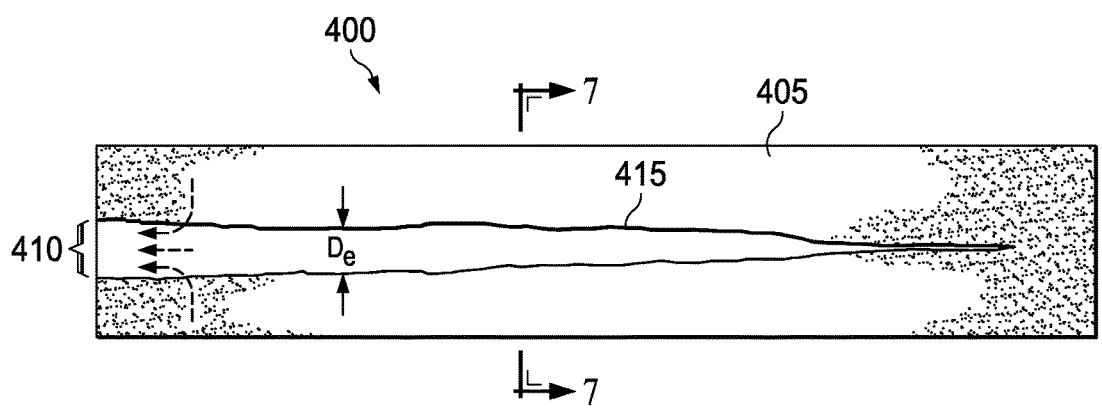
FIG. 6 is a second cross-sectional computerized tomography (CT) scan of an intact perforated core sample showing a cleared perforation tunnel.

FIG. 6 is a second cross-sectional computerized tomography (CT) scan of an intact perforated core sample 400 showing a cleared perforation tunnel 415. The second cross-sectional computerized tomography (CT) scan is at the same relative orientation as in FIG. 4, but of the cleared perforation tunnel 415 as per step 140 of FIG. 1. The effective diameter ($D_e$) is generally increased along the length of the perforation tunnel 415 by virtue of having removed the permeability-impairing material 450 illustrated in FIGS. 4 and 5. FIG. 7 is an alternative cross-sectional view of the second computerized tomography (CT) scan of the intact perforated core sample 400 showing the cleared perforation tunnel 415, taken through the line 7-7 in FIG. 6.

The ability of formation fluids to permeate the outer wall of the perforation tunnel 415 into the perforation tunnel 415 and out of the perforation 410 (thus, overall flow) would be expected to be increased in the condition of FIGS. 6 and 7, as compared with a perforation tunnel 415 in which the permeability-impairing material 450 is present like in the condition of FIGS. 4 and 5. Thus, a 3D mapping of the cleared tunnel will provide a useful comparison with a 3D mapping of the tunnel prior to clearing, in terms of assessing the potential influence of the permeability-impairing material in the perforation tunnel. In some embodiments, the second 3D model (e.g., step 180 of FIG. 1) may also be used to determine a geometry of the cleared perforation tunnel.

Figure 8:
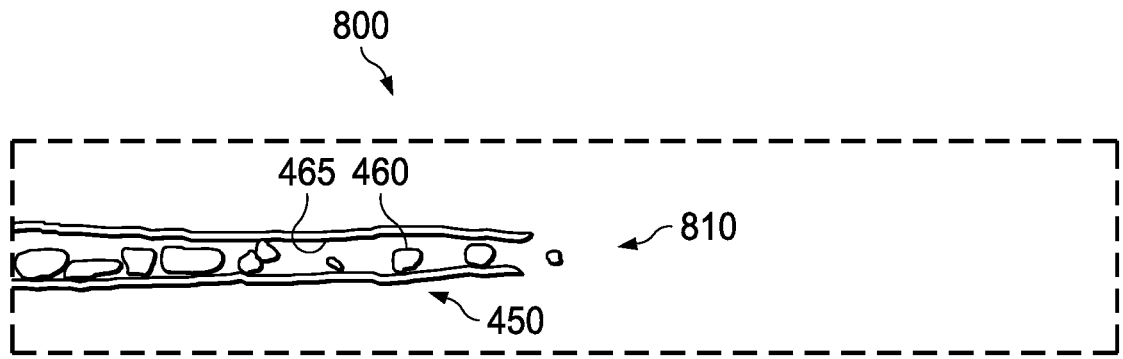
FIG. 8 is a cross-sectional 2-dimensional (2D) representation of a 3-dimensional (3D) mapping (which may exist in a computer model) of the true 3D variable-thickness profile of the permeability-impairing material (e.g. crushed zone material and the liner material) that lines the perforation tunnel.

More particularly, comparing the first and second 3D models or mappings may entail overlaying the first 3D model (e.g., from the first scan taken prior to clearing the perforation tunnel 415) and a second 3D model (e.g., from the second scan taken after clearing the perforation tunnel 415), wherein the two 3D models are at substantially the same orientation. To illustrate by example, FIG. 8 is a cross-sectional 2D representation of a 3D mapping 800 (which may exist in a computer model) of the true 3D variable-thickness profile 810 of the permeability-impairing material 450 (e.g. liner material 460 and the crushed zone material 465) that lines the perforation tunnel described above. Conceptually, as may be performed by a computer analytical model, the first 3D model represented by FIG. 4 and the second 3D model represented by FIG. 6 are at the same orientation, and may be overlaid by the analytical model, and the second 3D model subtracted from the first 3D model, to render a 3D mapping 800 of just the permeability-impairing material 450 of FIG. 4.

Further to the disclosure, the geometry (e.g., the second 3D model) of the cleared perforation tunnel may be used, in some examples, to calculate an idealized productivity index, which may be used in both analyses of the crush zone and also for determining a flow rate of the perforation tunnel. In one embodiment, the geometry of the cleared perforation tunnel may be used to determining a core flow efficiency (CFE) metric. The CFE metric, as discussed herein, is the ratio of an experimentally observed rate index of the perforated core sample to a post-shot "ideal" rate index of the same perforated core sample, where "ideal" as used in this paragraph means that the perforation tunnel is free of having any permeability-impairing material therein. CFE may be calculated by dividing the experimentally observed rate index of perforated core sample ($RI_{perf}$) by a theoretical ideal rate index ($RI_{th}$), where $RI_{th}$ is the theoretical rate index of an ideal perforated core sample. For example, the CFE of a clean, undamaged perforation tunnel is 1.0 and declines with the degree of damage from 1.0 to zero for a completely plugged condition of the perforation tunnel.

In some embodiments, the geometry of the perforation tunnel and of the crush zone may be used to determine a permeability value for the crush zone. Permeability (K) is a measure of a porous material's ability to allow fluids to pass through the porous material. Permeability (K) may be measured, for example, in darcies (d) or millidarcies (md). A porous medium has an absolute permeability of one darcy (d) when a single-phase fluid of one centipoise viscosity that completely fills the voids of the medium will flow through it under conditions of viscous flow at a rate of 1 cm$^3$/s per 1 cm$^2$ bulk cross-sectional area under a pressure or equivalent fluid potential gradient of one atmosphere per centimeter. Permeability is important for determining fluid flow in a reservoir; especially directional permeability since reservoir fluid flow is 3D. As such, measurement of a rock core sample's permeability (e.g., in the direction of pressure gradient) can be beneficial in various stages of well planning and preparation, including but not limited to forecasting well performance and construction and completion planning for a well. Embodiments will be discussed herein which provide for determining a permeability of a crush zone of a perforated core sample.

Figure 9:
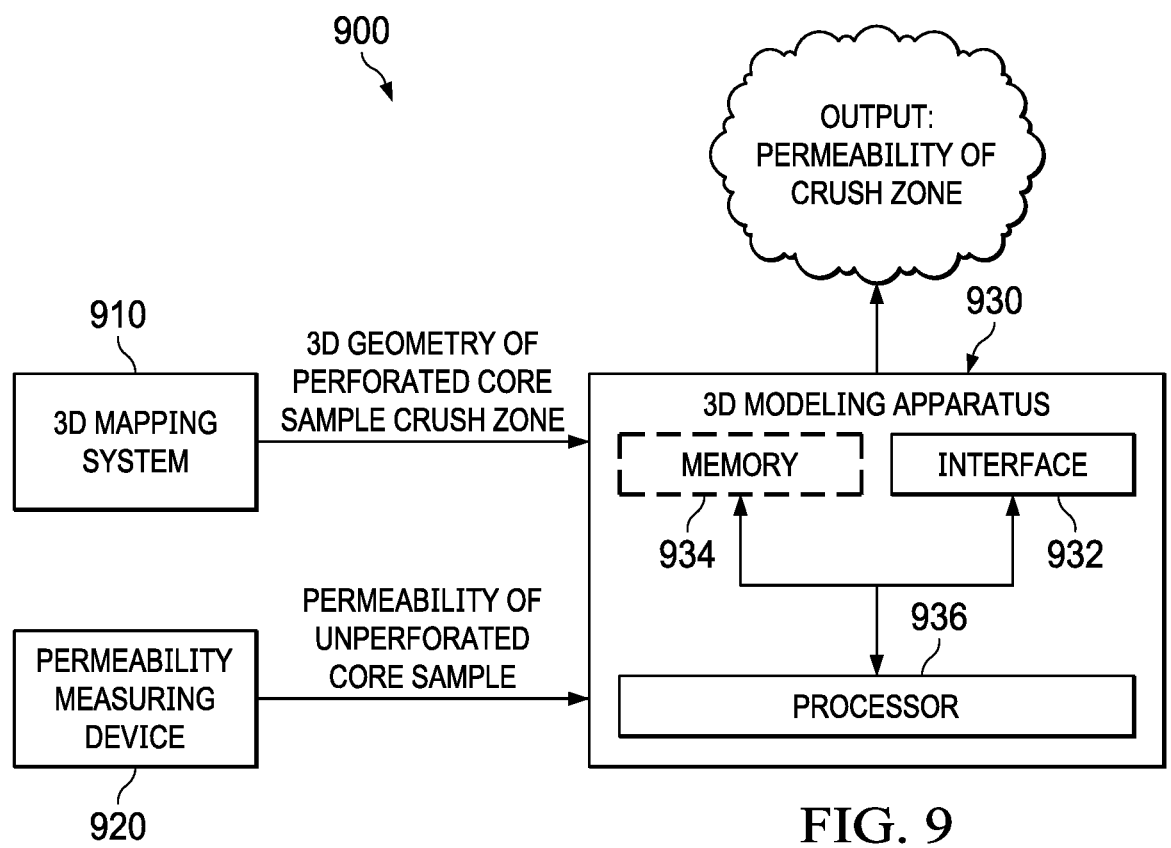
FIG. 9 is a block diagram of one embodiment of a 3D modeling system for determining a permeability of a crush zone of a perforated core sample.

FIG. 9 is a block diagram of one embodiment of a 3D modeling system 900 for determining a permeability of a crush zone of a perforated core sample. The 3D modeling system may also be used for mapping a perforation tunnel and crush zone of a perforated core sample, such as discussed above with regard to FIGS. 1-8. The 3D modeling system 900 may be used to estimate a permeability value, $k_c$, for the crush zone using 3D mapping inputs and 3D modeling information. The permeability value $k_c$ may provide a more accurate permeability value than crush zone permeability values determined using only one or two dimensional modeling information. The one and two dimensional modeling calculations rely upon manual thickness measurements for the geometry of the crush zone, and use estimated or assumed values for unmeasured geometric parameters. The resulting permeability value $k_c$ for the crush zone generated using 3D mapping inputs can be used for well site planning or operations, such as production planning for a well site.

The 3D modeling system 900 may include a 3D mapping system 910, a permeability measuring device 920, and a 3D modeling apparatus 930. The 3D mapping system 910 is configured to provide a 3D mapping of at least a crush zone of a perforated core sample. The 3D mapping system 910 may include one or more computerized tomography (CT) scanning devices for scanning a perforated core sample to obtain 3D models of the perforated core sample as discussed above with respect to method 100 and FIG. 1. The permeability measuring device 920 is configured to measure the permeability of the core sample before perforation. The permeability measuring device 920 may be a traditional device used for measuring the permeability of a core sample. In some examples, the permeability measuring device 920 may be a device configured to measure the permeability in the direction of pressure gradient, wherein the core sample is placed, unbounded or uninsulated, between an inlet flow plate and an outlet flow plate, where after fluid is directed through the inlet flow plate into the core sample, and a flow rate of fluid exiting the outlet flow plate is measured.

The 3D modeling apparatus 930 is configured to (e.g., designed to perform a designated instruction, task or function) estimate the permeability of the crush zone. The 3D modeling apparatus 930, or at least a portion thereof, may be embodied as a series of operating instructions stored on a non-transitory computer-readable medium that direct the operation of a processor when initiated. The 3D modeling apparatus 930 may be stored on a single computer or on multiple computers. A portion of the 3D modeling apparatus 930 may be located on a server and other portions of 3D modeling apparatus 930 can be located on a computing device or devices that are connected to the server via a network or networks. In some embodiments, the 3D modeling apparatus 930 may be housed on a network, or may be stored at another computer storage facility. In one embodiment, the 3D modeling apparatus 930 is implemented on a server that includes the necessary logic and memory to perform the functions disclosed herein, e.g., to estimate the permeability of the crush zone. Accordingly, the 3D modeling apparatus 930 may also be a website hosted on a web server, or servers, and that is accessible via the World Wide Web, wherein a Uniform Resource Locator (URL) may be used to access various aspects of the 3D modeling apparatus 930. The various components of the 3D modeling apparatus 930 may communicate via wireless or wired connections.

The 3D modeling apparatus 930 may include at least one interface 932, a memory 934 and a processor 936. The interface 932 is a component or device interface configured to receive inputs either manually from a user or as inputs from one or more devices coupled thereto. The interface 932 may be configured to receive inputs associated with a core sample, such as, a 3D mapping of a crush zone and a permeability of the core sample, from at least the 3D mapping system 910 and the permeability measuring device 920.

The memory 934 is configured to store the various software aspects related to the 3D modeling apparatus 930. Additionally, the memory 934 may be configured to store a series of operating instructions that direct the operation of the processor 936 when initiated. The memory 934 may be a non-transitory computer readable medium, and in some embodiments, may be the memory of a server.

The processor 936 may be configured to direct the operation of the 3D modeling apparatus 930 and to estimate the permeability of the crush zone based upon the permeability of the core sample and the 3D mapping. As such, the processor 936 includes the necessary logic to communicate with the interface 932 and the memory 934 and perform the functions described herein to generate an output. In one embodiment, the output is a permeability for a crush zone (10 of a perforated core sample based on inputs, including a 3D mapping of the crush zone, received by the 3D modeling apparatus 930. The processor 936 may be configured to perform at least some steps of a method for determining a permeability of a crush zone using 3D mapping inputs and 3D modeling information, such as method 1000 discussed below. In some embodiments, the processor 936 may be part of a server.

Figure 10:
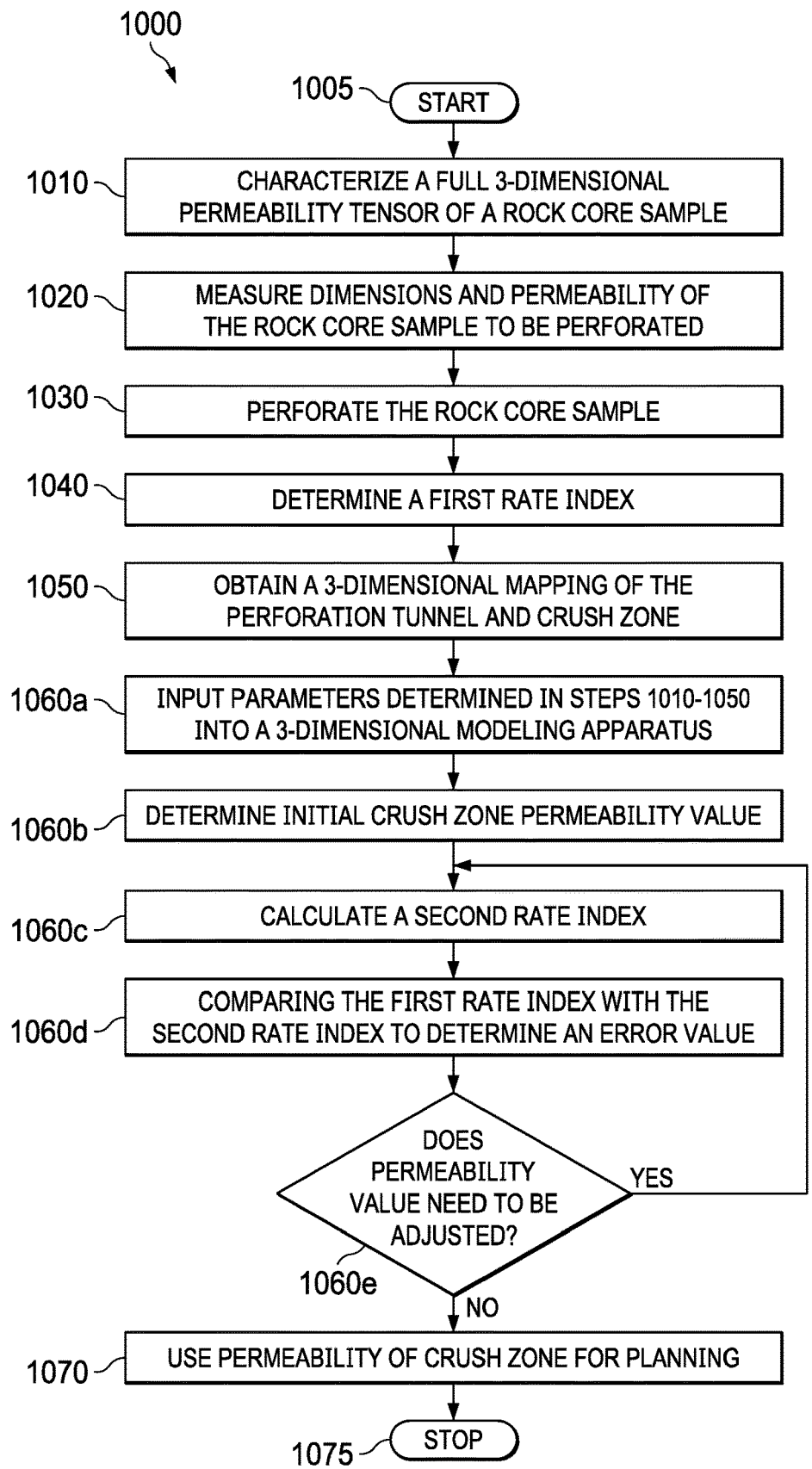
FIG. 10 illustrates a flow chart of a method for determining a permeability of a crush zone of a perforated core sample using a 3D modeling apparatus according to the disclosure.

FIG. 10 illustrates a flow chart of a method 1000 for determining parameters of a perforated core sample using a 3D modeling apparatus according to the disclosure. For example, the 3D modeling apparatus 930 may provide an estimate of the permeability of a crush zone by employing an algorithm corresponding to at least some of the steps of the method 1000. The permeability of certain portions of a perforated core sample, including the crush zone, may help provide information when planning and forecasting well performance, including expected flow rate. In some embodiments, in order to model permeability of the crush zone, certain inputs may be needed, including a permeability value of the core sample measured prior to perforating the core sample. The permeability of the core sample may be measured by traditional methods or by measuring the permeability in the direction of pressure gradient as discussed above. The method 1000 begins in a start step 1005.

In a step 1010, a full 3D permeability tensor of an unperforated core sample is characterized prior to the core sample being perforated in order to calculate certain values when determining the permeability of the crush zone. Some characteristics of the permeability tensor include three principal permeability coefficients and their orientations. Anisotropic permeability is considered to be a symmetric $2^{nd}$-rank positive-definite tensor. The general absolute Darcy permeability tensor $\bar{k}_d$ is represented by a 3×3 matrix of scalars, which in an arbitrarily selected 3D Cartesian coordinate system is written as Equation 1:

$$\bar{k}_d = \begin{bmatrix} k_{d,xx} & k_{d,xy} & k_{d,xz} \\ k_{d,yx} & k_{d,yy} & k_{d,yz} \\ k_{d,zx} & k_{d,zy} & k_{d,zz} \end{bmatrix} \quad (1)$$

The permeability tensor is symmetric and as such, $k_{d,ij} = k_{d,ji}$ (i,j=x,y,z or 1,2,3 or $x_1, x_2, x_3$). The diagonal coefficients are generally referred to as the normal permeability coefficients, and the off-diagonal coefficients are referred to as the cross permeability coefficients. One important property of a symmetric permeability tensor is that by a suitable rotation of the chosen coordinate system axes, it is possible to transform the full tensor into another tensor consisting of only diagonal terms. The axes that permit this transformation are called the principal axes (the eigenvectors of the tensor). These principal axes contain the maximum, intermediate, and minimum values of the directional permeabilities. These are the diagonal terms of the transformed tensor (the eigenvalues of the tensor). Thus, when the x, y, z axes of the 3D Cartesian coordinate system are co-linear with the principal directions of permeability anisotropy, the 3D permeability tensor is calculated, in one embodiment, according to the following equation, Equation 2:

$$\bar{k}'_d = \begin{bmatrix} k'_{d,x} & 0 & 0 \\ 0 & k'_{d,y} & 0 \\ 0 & 0 & k'_{d,z} \end{bmatrix} \quad (2)$$

In a step 1020, dimensions of the unperforated core sample are measured. At least two dimensions are needed. In some embodiments, the unperforated core sample may be a cylinder shape and the dimensions may include a core length (L) and a diameter (D), such as shown above with regard to FIG. 1. In other embodiments, the unperforated core sample may have other shapes and dimensions, such as surface area (SA) and thickness (T). In this example, the dimensions discussed will include an unperforated core sample length (L) and diameter (D). In a step 1030, a perforated core sample may be obtained. The perforated core sample may be perforated according to traditional perforation methods, e.g., by following American Petroleum Institute (API) Recommended Practice (RP) 19B, Section 2 and Section 4, or other suitable methods for perforation for testing purposes as discussed above.

In one example, the perforated core sample is obtained by perforating a different unperforated core sample than the unperforated core sample discussed above with respect to steps 1010 and 1020. In one or more other examples, the different unperforated core sample and the unperforated core samples discussed above with respect to steps 1010 and 1020 have similar permeability properties, and thus are representative of one another. In one or more different examples, the different unperforated core sample and the unperforated core samples discussed above with respect to steps 1010 and 1020 were originally obtained from the same formation, and thus have similar starting properties are representative of one another. However, in one or more examples, the perforated core sample and the unperforated core sample are representative of one another as the perforated core sample is obtained by perforating the unperforated core sample discussed above with respect to steps 1010 and 1020.

In a step 1040, a first rate index of the perforated core sample is determined. The first rate index can be an experimentally observed rate index ($RI_{perf}$) of the perforated core sample. The experimentally observed rate index is an experimentally observed "true" rate index of the perforation. In one embodiment, the experimentally observed rate index of the perforated core sample may be experimentally determined under axial pressure-flow boundary conditions. Per API 19B Sections 2 and 4, the axial pressure-flow boundary condition may be defined as having a pore pressure uniformly distributed at the unperforated end (B) (as shown in FIG. 4) of the perforated core sample, while the flow rate crossing the radial and perforated end (A) of the perforated core sample is about zero.

In other embodiments, the experimentally observed rate index of the perforated core sample may be experimentally determined in semi-radial pressure-flow boundary conditions. A semi-radial pressure-flow boundary condition may be defined as having a constant pressure boundary condition on the perforated core sample's entire radial surface, and no-flow boundary conditions on the perforated end (A) and unperforated end (B) of the perforated core sample.

In other embodiments, the experimentally observed rate index of the perforated core sample may be experimentally determined under axi-radial pressure-flow boundary conditions. An axi-radial pressure-flow boundary condition is the combination of the axial and semi-radial pressure-flow boundary conditions, wherein a constant pressure boundary condition is applied on both the perforated core sample's entire radial surface and at its unperforated end (B), and a no-flow boundary condition is applied on its perforated end (A).

In one example, the traditional method for determining the experimentally observed rate index may include, the API RP 19B, Section 4 testing methodology. As discussed herein, the term "rate index" ("RI") may be used as a general term used in place of the commonly used terms "productivity index" and "injectivity index", which may denote the direction of the flow with respect to the orientation of the perforation. Mathematically, the rate index (RI) may be defined as the volumetric flow rate (q) divided by the difference in fluid potential (e.g. pressure) driving the flow ($\Delta\Phi$): [RI=q/$\Delta\Phi$]. More generally, to account for varying fluid viscosities and densities, the experimentally observed rate index ($RI_{perf}$) may be an in-situ viscosity-corrected rate index, and may be determined according to the following equation: [$RI_{perf}$=qu/$\Delta\Phi$].

After the first rate index is determined, the 3D mapping (e.g., geometries and dimensions) of the perforation tunnel and crush zone of the perforated core sample are obtained in a step 1050. In some embodiments, the 3D mapping of the perforation tunnel and crush zone may be obtained according to the method discussed above in conjunction with FIGS. 1-8. In other embodiments, the 3D mapping of the perforation tunnel and crush zone may be provided or obtained according to another method or source, or may be provided by a user of the 3D modeling apparatus.

After steps 1010 through 1050 are completed, the following five parameters may now be available for the perforated core sample: 1) the three principal permeability coefficients and their orientations of the unperforated core sample; 2) the unperforated core sample's dimensions; 3) the experimentally observed rate index of the perforated core sample ($RI_{perf}$); 4) a first 3D image and model of the perforation tunnel wall (prior to removal of the crush zone permeability impairing-material); and 5) a second 3D image and model of the cleared perforation tunnel.

In a next series of steps 1060a through 1060e, at least some of the foregoing parameters may be used for determining a virtual model or 3D model of the perforated core sample and for determining the permeability of the crush zone. Other parameters in addition to the five parameters noted above may also be employed. In some embodiments, the parameters may be input into a fluid dynamics modeling tool, such as a computational fluid dynamics (CFD) modeling tool, in a step 1060a, to build a virtual 3D model of the perforated core sample. The virtual 3D model of the perforated core sample may then be used to determine the simulated rate index of perforated rock under various pressure-flow boundary conditions.

In a step 1060b, an initial permeability value $k_c$ for the crush zone is determined. In one embodiment, the initial permeability value $k_c$ may be an effective-isotropic permeability value, and may be determined according to an initial educated guess based on the previously obtained parameters of the core sample. Regardless of how it is determined, the initial permeability value $k_c$ needs to be greater than zero for step 1060b. In some examples, the initial permeability value may be based on the user's knowledge of the virgin rock from which the core sample is taken. In other embodiments, the initial permeability value $k_c$ may be a geometrical average of permeabilities of the virgin rock from with the core sample, taken along the x, y, and z axes, which may be calculated by the following equation, Equation 3:

$$\bar{k}_c = [d'_{dx} \cdot k'_{dy} \cdot k'_{az}]^{1/3} \quad (3)$$

In a step 1060c, a second rate index is determined. The second rate index can be a simulated rate index ($RI_{sim}$) that is calculated applying the same set of pressure-flow boundary conditions as used in step 1040 to calculate the experimentally observed rate index ($RI_{perf}$), using the computational fluid dynamics modeling tool. The simulated rate index ($RI_{sim}$) is a calculated rate index based on the modeling inputs and virtual model built above in steps 1060a and 1060b.

In a next step 1060d, a difference, or error, between the first and second rate indexes is calculated. For example, a true error between the simulated rate index ($RI_{sim}$) and the experimentally observed rate index ($RI_{perf}$) is calculated. A True Error value ($E_t$) equals True Value (experimentally observed rate index) minus Approximation (simulated rate index), which is represented by the following equation, Equation 4:

$$E_t = \text{True Value}(RI_{perf}) - \text{Approximation}(RI_{sim}). \quad (4)$$

To account for an order of magnitude of the True Value under examination, the True Error value may be normalized, as represented by the Equation 5:

$$\text{True fractional relative error} = (\text{True Value} - \text{Approximation})/\text{True Value} \quad (5)$$

The True fractional relative error may then be converted into a percentage ($e_t$) using, for example, Equation 6:

$$e_t = [(\text{True Value} - \text{Approximation})/\text{True Value}]*100\%. \quad (6)$$

In a next step 1060e, a determination is made whether the value assigned to the model's crush zone permeability may need to be adjusted. In one example, the difference, or error, between the simulated rate index and the experimentally observed rate index is compared against a Specified Error tolerance ($e_s$) (expressed as a percent of error) to determine if the adjustment is needed. A user or engineer planning downhole production requirements for wellbore may have a certain error tolerance desired for the analysis. Accordingly, the Specified Error tolerance ($e_s$) may be determined by the user. In some embodiments, the acceptable Specified Error tolerance ($e_s$) may be as low as or less than 0.01%. In other embodiments, the acceptable Specified Error tolerance ($e_s$) may be less than 1%. The acceptable Specified Error tolerance ($e_s$) may be up to 5%, or in some cases, as high as up to 10%. Other values, including higher values of the acceptable Specified Error tolerance ($e_s$), may be applied according to, for example, user preferences, well site locations, well drilling and production planning stages, etc. For example, the value of the acceptable Specified Error tolerance ($e_s$) may be determined based upon whether there may be an environmental issue at a well site or a safety issue at the well site. In one example, the greater the safety risk, the lower the acceptable Specified Error tolerance ($e_s$).

When the permeability value needs to be adjusted, then the method 1000 returns to step 1060c. For example, if $e_t$ is greater than $e_s$ ($e_t \geq e_s$), then the permeability value $k_c$ value for the crush zone may be adjusted (e.g., by selecting a subsequent permeability value of the crush zone) and steps 1060c through 1060d are repeated. When the permeability value does not need to be adjusted, then the method 1000 continues to step 1070. For example, when the difference, or error, between the simulated rate index and the experimentally observed rate index is such that $e_t$ is less than $e_s$, ($e_t < e_s$), then the difference or error is considered "insignificant" and the last permeability value $k_c$ is the determined permeability value for the crush zone.

In step 1070, the determined permeability value $k_c$ for the crush zone is used for well site planning. The determined permeability value $k_c$ may be provided to a user of the 3D modeling apparatus and used for planning. The permeability value $k_c$ may be used in various aspects of well drilling and production planning, including estimating a more accurate expected output of a well. The method may then end at a step 1075.

A portion of the above-described apparatus, systems or methods may be embodied in or performed by various analog or digital data processors, wherein the processors are programmed or store executable programs of sequences of software instructions to perform one or more of the steps of the methods. A processor may be, for example, a programmable logic device such as a programmable array logic (PAL), a generic array logic (GAL), a field programmable gate arrays (FPGA), or another type of computer processing device (CPD). In some applications, the processor can be part of a server. The software instructions of such programs may represent algorithms and be encoded in machine-executable form on non-transitory digital data storage media, e.g., magnetic or optical disks, random-access memory (RAM), magnetic hard disks, flash memories, and/or read-only memory (ROM), to enable various types of digital data processors or computers to perform one, multiple or all of the steps of one or more of the above-described methods, or functions, systems or apparatuses described herein.

Portions of disclosed embodiments may relate to computer storage products with a non-transitory computer-readable medium that have program code thereon for performing various computer-implemented operations that embody a part of an apparatus, device or carry out the steps of a method set forth herein. Non-transitory used herein refers to all computer-readable media except for transitory, propagating signals. Examples of non-transitory computer-readable media include, but are not limited to: magnetic media such as hard disks, floppy disks, and magnetic tape; optical media such as CD-ROM disks; magneto-optical media such as optical disks; and hardware devices that are specially configured to store and execute program code, such as ROM and RAM devices. Examples of program code include machine code, such as produced by a compiler, and files containing higher level code that may be executed by the computer using an interpreter.

In interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Those skilled in the art to which this application relates will appreciate that other and further additions, deletions, substitutions and modifications may be made to the described embodiments. It is also to be understood that the terminology used herein is for the purpose of describing particular embodiments only, and is not intended to be limiting, since the scope of the present disclosure will be limited only by the claims. Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, a limited number of the exemplary methods and materials are described herein.

It is noted that as used herein and in the appended claims, the singular forms "a", "an", and "the" include plural referents unless the context clearly dictates otherwise.

Aspects disclosed herein include:

A. A method for mapping a perforation tunnel and crush zone of a perforated core sample, the method including: 1) scanning a perforated core sample having a perforation tunnel containing a permeability-impairing material with a first computerized tomography (CT) scanning apparatus to produce a first 3D model of the perforation tunnel; 2) forming a cleared perforation tunnel by removing at least a portion of the permeability-impairing material from within the perforation tunnel without splitting the core sample at the perforation tunnel; 3) scanning the perforated core sample having the cleared perforation tunnel with a second computerized tomography (CT) scanning apparatus to produce a second 3D model of the cleared perforation tunnel; and 4) comparing the first 3D model and the second 3D model to obtain a 3D mapping of the perforation tunnel or a crush zone.

B. A method for determining a permeability of a crush zone of a perforated core sample, the method including: 1) mapping a perforation tunnel and crush zone of a perforated core sample, including; a) scanning a perforated core sample having a perforation tunnel containing a permeability-impairing material with a first computerized tomography (CT) scanning apparatus to produce a first 3D model of the perforation tunnel; b) forming a cleared perforation tunnel by removing the permeability-impairing material from within the perforation tunnel without splitting the core sample at the perforation tunnel; c) scanning the perforated core sample having the cleared perforation tunnel with a second computerized tomography (CT) scanning apparatus to produce a second 3D model of the cleared perforation tunnel; and d) comparing the first 3D model and the second 3D model to obtain a 3D mapping of a crush zone; and 2) determining a permeability value for the crush zone based on a permeability of an unperforated core sample and the 3D mapping of the crush zone of the perforated core sample.

Aspects A, B, and C may have one or more of the following additional elements in combination: Element 1: wherein comparing the first 3D model and the second 3D model comprises overlaying the first and second 3D models using the same orientation. Element 2: further comprising subtracting one of the 3D models from the other of the 3D models to obtain a variable-thickness profile of the permeability-impairing material. Element 3: wherein removing the permeability-impairing material includes removing one or both of a liner material originating from a jet of a shaped charge used to form the perforation tunnel and a crushed-zone material lining the perforation tunnel. Element 4: wherein removing the permeability-impairing material includes removing the permeability-impairing material using a rotary tool having a brush attached thereto. Element 5: wherein removing the permeability-impairing material using a rotary tool having a brush attached thereto includes sweeping the brush into and out of the perforation tunnel while the rotary tool rotates the brush. Element 6: further including obtaining an unaltered core sample, determining a permeability of the unaltered core sample, and then perforating the unaltered core sample to form the perforated core sample having the perforation tunnel. Element 7: wherein further including flushing the perforated core sample having the perforation tunnel with a fluid prior to scanning the perforated core sample with the first computerized tomography (CT) scanning apparatus. Element 8: wherein flushing the perforated core sample having the perforation tunnel with a fluid includes flushing the perforated core sample having the perforation tunnel with a gas or liquid sufficient to remove loose permeability-impairing material residing within the perforation tunnel. Element 9: wherein scanning the perforated core sample having the perforation tunnel containing the permeability-impairing material with the first computerized tomography (CT) scanning apparatus and scanning the perforated core sample having the cleared perforation tunnel with the second computerized tomography (CT) scanning apparatus includes scanning the perforated core sample having the perforation tunnel and scanning the perforated core sample having the cleared perforation tunnel using a same computerized tomography (CT) scanning apparatus. Element 10: wherein forming a cleared perforation tunnel includes forming a cleared perforation tunnel having greater than 75% by volume of the permeability impairing material removed therefrom. Element 11: wherein forming a cleared perforation tunnel includes forming a cleared perforation tunnel having greater than 75% by volume of the permeability impairing material removed therefrom. Element 12: further including determining a geometry of the perforation tunnel using one or both of the first and second 3D models. Element 13: wherein determining a geometry of the perforation tunnel using one or both of the first and second 3D models, including determining a geometry of the cleared perforation tunnel using the second 3D model. Element 14: further including calculating an idealized productivity index from the geometry of the cleared perforation tunnel. Element 15: further including calculating a core flow efficiency (CFE) metric of the cleared perforation tunnel. Element 16: wherein calculating the core flow efficiency (CFE) metric includes dividing an experimentally observed rate index of the perforated core sample ($RI_{perf}$) by a theoretical ideal rate index ($RI_{th}$) of an ideal perforated core sample. Element 17: wherein determining the permeability value for the crush zone includes: calculating an experimentally observed rate index using the permeability of the unperforated core sample and the 3D mapping of the crush zone; selecting an initial permeability value of the crush zone; calculating a simulated rate index of the perforated core sample using the initial permeability value of the crush zone; calculating an error value between the simulated rate index and the experimentally observed rate index; and comparing the error value with a specified error tolerance. Element 18: further including determining a geometry of the perforation tunnel using the second 3D model and calculating a core flow efficiency of the perforated core sample using the geometry of the perforation tunnel. Element 19: wherein determining the permeability value for the crush zone of the perforated core sample includes: 1) calculating an experimentally observed rate index using the permeability of the representative unperforated core sample and the 3D mapping of the crush zone of the perforated core sample; 2) selecting an initial permeability value of the crush zone of the perforated core sample; 3) calculating a simulated rate index of the perforated core sample using the initial permeability value of the crush zone of the perforated core sample; 4) calculating an error value between the simulated rate index and the experimentally observed rate index; and 5) comparing the error value with a specified error tolerance. Element 20: wherein determining the permeability value for the crush zone of the perforated core sample further includes: 1) selecting a subsequent permeability value of the crush zone of the perforated core sample; 2) re-calculating the simulated rate index of the perforated core sample using the subsequent permeability value of the crush zone of the perforated core sample, and 3) re-calculating the error value until the error value between the simulated rate index and the experimentally observed rate index is less than the specified error tolerance. Element 21: wherein the experimentally observed rate index and the simulated rate index are calculated under a pressure-flow boundary condition. Element 22: wherein the pressure-flow boundary condition is one of an axial pressure-flow boundary condition, a semi-radial pressure-flow boundary condition, or an axi-radial pressure-flow boundary condition. Element 23: wherein the initial permeability value of the crush zone of the perforated core sample is an effective-isotropic permeability value. Element 24: wherein calculating the experimentally observed rate index and the simulated rate index includes using a fluid dynamics modeling tool. Element 25: wherein the specified error tolerance is selected based on a safety issue or an environmental issue at a well site. Element 26: wherein providing a 3D mapping of the crush zone of the perforated core sample includes: 1) scanning a perforated core sample having a perforation tunnel containing a permeability-impairing material with a first computerized tomography (CT) scanning apparatus to produce a first 3D model of the perforation tunnel; 2) forming a cleared perforation tunnel by removing at least a portion of the permeability-impairing material from within the perforation tunnel without splitting the core sample at the perforation tunnel; 3) scanning the perforated core sample having the cleared perforation tunnel with a second computerized tomography (CT) scanning apparatus to produce a second 3D model of the cleared perforation tunnel; and 4) comparing the first 3D model and the second 3D model to obtain a 3D mapping of the perforation tunnel or the crush zone of the perforated core sample. Element 27: further including determining a geometry of the perforation tunnel using the second 3D model and calculating a core flow efficiency of the perforated core sample using the geometry of the perforation tunnel. Element 28: wherein the permeability of the representative core sample is a permeability of the core sample determined before perforation, and further wherein the processor is configured to estimate the permeability of the crush zone of the perforated core sample by: 1) calculating an experimentally observed rate index using the permeability of the core sample determined before perforation and the 3D mapping of the crush zone of the perforated core sample; 2) selecting an initial permeability value of the crush zone of the perforated core sample; 3) calculating a simulated rate index of the perforated core sample using the initial permeability value of the crush zone of the perforated core sample; 4) calculating an error value between the simulated rate index and the experimentally observed rate index; and 5) comparing the error value with a specified error tolerance. Element 29: wherein the processor is further configured to estimate the permeability of the crush zone of the perforated core sample by: 1) selecting a subsequent permeability value of the crush zone of the perforated core sample; 2) re-calculating the simulated rate index using the subsequent permeability value of the crush zone of the perforated core sample; and 3) re-calculating the error value until the error value between the simulated rate index and the experimentally observed rate index is less than the specified error tolerance. Element 30: wherein the initial permeability value of the crush zone of the perforated core sample is an effective-isotropic permeability value. Element 31: wherein calculating the experimentally observed rate index and the simulated rate index includes using a fluid dynamics modeling tool. Element 32: wherein estimating the permeability of the crush zone of the perforated core sample includes: 1) calculating an experimentally observed rate index using the permeability of the core sample determined before perforation and the 3D mapping of the crush zone of the perforated core sample; 2) selecting an initial permeability value of the crush zone of the perforated core sample; and 3) calculating a simulated rate index of the perforated core sample using the initial permeability value of the crush zone of the perforated core sample. Element 33: wherein estimating the permeability of the crush zone of the perforated core sample further includes: 1) calculating an error value between the simulated rate index and the experimentally observed rate index; 2) comparing the error value with a specified error tolerance; and 3) selecting a subsequent permeability value of the crush zone of the perforated core sample. Element 34: wherein estimating the permeability of the crush zone of the perforated core sample further includes: 1) re-calculating the simulated rate index, and 2) re-calculating the error value until the error value between the simulated rate index and the experimentally observed rate index is less than the specified error tolerance. Element 35: wherein the initial permeability value of the crush zone of the perforated core sample is an effective-isotropic permeability value.

Further additions, deletions, substitutions and modifications may be made to the described embodiments.

What is claimed is:
1. A method for mapping a perforation tunnel and crush zone of a perforated core sample, the method comprising:
   scanning a perforated core sample having a perforation tunnel containing a permeability-impairing material with a first computerized tomography (CT) scanning apparatus to produce a first 3D model of the perforation tunnel;
   forming a cleared perforation tunnel by removing at least a portion of the permeability-impairing material from within the perforation tunnel without splitting the core sample at the perforation tunnel;
   scanning the perforated core sample having the cleared perforation tunnel with a second computerized tomography (CT) scanning apparatus to produce a second 3D model of the cleared perforation tunnel; and
   comparing the first 3D model and the second 3D model to obtain a 3D mapping of the perforation tunnel or a crush zone.

2. The method according to claim 1, wherein comparing the first 3D model and the second 3D model comprises overlaying the first and second 3D models using the same orientation.

3. The method according to claim 2, further comprising subtracting one of the 3D models from the other of the 3D models to obtain a variable-thickness profile of the permeability-impairing material.

4. The method according to claim 1, wherein removing the permeability-impairing material includes removing one or both of a liner material originating from a jet of a shaped charge used to form the perforation tunnel and a crushed-zone material lining the perforation tunnel.

5. The method according to claim 1, wherein removing the permeability-impairing material includes removing the permeability-impairing material using a rotary tool having a brush attached thereto.

6. The method according to claim 5, wherein removing the permeability-impairing material using a rotary tool having a brush attached thereto includes sweeping the brush into and out of the perforation tunnel while the rotary tool rotates the brush.

7. The method according to claim 1, further including obtaining an unaltered core sample, determining a permeability of the unaltered core sample, and then perforating the unaltered core sample to form the perforated core sample having the perforation tunnel.

8. The method according to claim 7, further including flushing the perforated core sample having the perforation tunnel with a fluid prior to scanning the perforated core sample with the first computerized tomography (CT) scanning apparatus.

9. The method according to claim 8, wherein flushing the perforated core sample having the perforation tunnel with a fluid includes flushing the perforated core sample having the perforation tunnel with a gas or liquid sufficient to remove loose permeability-impairing material residing within the perforation tunnel.

10. The method according to claim 1, wherein scanning the perforated core sample having the perforation tunnel containing the permeability-impairing material with the first computerized tomography (CT) scanning apparatus and scanning the perforated core sample having the cleared perforation tunnel with the second computerized tomography (CT) scanning apparatus includes scanning the perforated core sample having the perforation tunnel and scanning the perforated core sample having the cleared perforation tunnel using a same computerized tomography (CT) scanning apparatus.

11. The method according to claim 1, wherein forming a cleared perforation tunnel includes forming a cleared perforation tunnel having greater than 75% by volume of the permeability impairing material removed therefrom.

12. The method according to claim 1, wherein forming a cleared perforation tunnel includes forming a cleared perforation tunnel having greater than 75% by volume of the permeability impairing material removed therefrom.

13. The method according to claim 1, further including determining a geometry of the perforation tunnel using one or both of the first and second 3D models.

14. The method according to claim 13, wherein determining a geometry of the perforation tunnel using one or both of the first and second 3D models, including determining a geometry of the cleared perforation tunnel using the second 3D model.

15. The method according to claim 14, further including calculating an idealized productivity index from the geometry of the cleared perforation tunnel.

16. The method according to claim 15, further including calculating a core flow efficiency (CFE) metric of the cleared perforation tunnel.

17. The method according to claim 16, wherein calculating the core flow efficiency (CFE) metric includes dividing an experimentally observed rate index of the perforated core sample ($RI_{perf}$) by a theoretical ideal rate index ($RI_{th}$) of an ideal perforated core sample.

18. A method for determining a permeability of a crush zone of a perforated core sample, the method comprising:
 mapping a perforation tunnel and crush zone of a perforated core sample, including;
  scanning a perforated core sample having a perforation tunnel containing a permeability-impairing material with a first computerized tomography (CT) scanning apparatus to produce a first 3D model of the perforation tunnel;
  forming a cleared perforation tunnel by removing the permeability-impairing material from within the perforation tunnel without splitting the core sample at the perforation tunnel;
  scanning the perforated core sample having the cleared perforation tunnel with a second computerized tomography (CT) scanning apparatus to produce a second 3D model of the cleared perforation tunnel; and
  comparing the first 3D model and the second 3D model to obtain a 3D mapping of a crush zone; and
 determining a permeability value for the crush zone based on a permeability of an unperforated core sample and the 3D mapping of the crush zone of the perforated core sample.

19. The method according to claim 18, wherein determining the permeability value for the crush zone includes:
 calculating an experimentally observed rate index using the permeability of the unperforated core sample and the 3D mapping of the crush zone;
 selecting an initial permeability value of the crush zone;
 calculating a simulated rate index of the perforated core sample using the initial permeability value of the crush zone;
 calculating an error value between the simulated rate index and the experimentally observed rate index; and
 comparing the error value with a specified error tolerance.

20. The method according to claim 18, further including determining a geometry of the perforation tunnel using the second 3D model and calculating a core flow efficiency of the perforated core sample using the geometry of the perforation tunnel.

* * * * *

UNITED STATES PATENT AND TRADEMARK OFFICE
CERTIFICATE OF CORRECTION

PATENT NO. : 10,908,314 B1  
APPLICATION NO. : 16/787545  
DATED : February 2, 2021  
INVENTOR(S) : Jacob Andrew McGregor Page 1 of 1

It is certified that error appears in the above-identified patent and that said Letters Patent is hereby corrected as shown below:

In the Specification

In Column 7, Line 32, delete "(10" and insert --($k_c$)--

Signed and Sealed this  
Fourth Day of May, 2021

Drew Hirshfeld  
*Performing the Functions and Duties of the*  
*Under Secretary of Commerce for Intellectual Property and*  
*Director of the United States Patent and Trademark Office*